United States Patent [19]

Humphrey et al.

[11] 4,205,676
[45] Jun. 3, 1980

[54] AIR PUMPING FOR MEDICAL USES

[75] Inventors: Delby C. Humphrey, Terre Haute, Ind.; Benjamin R. Wimer, Mathews, Va.

[73] Assignee: Deley C. Humphrey, Terre Haute, Ind.

[21] Appl. No.: 885,699

[22] Filed: Mar. 13, 1978

[51] Int. Cl.² ............................................. A61J 7/00
[52] U.S. Cl. ................................................... 128/222
[58] Field of Search ............. 128/1 R, 172, 213, 222, 128/223–225, 230–231, 232, 260, 262, 348, 349 R, 349 B, DIG. 1, DIG. 12; 222/94, 386.5

[56] References Cited

U.S. PATENT DOCUMENTS

| | | | |
|---|---|---|---|
| 1,956,006 | 4/1934 | Coons | 128/225 |
| 2,596,947 | 5/1952 | Turkel | 128/348 |
| 3,289,891 | 12/1966 | Frankenberg | 222/386.5 |
| 3,391,830 | 7/1968 | Kitchens | 128/222 |
| 3,894,538 | 7/1975 | Richter | 128/260 |
| 4,041,944 | 8/1977 | Rhodes | 128/DIG. 12 |
| 4,048,994 | 9/1977 | Lo | 128/DIG. 12 |
| 4,090,514 | 5/1978 | Hinck et al. | 128/DIG. 12 |

FOREIGN PATENT DOCUMENTS 2345141  11/1977  France .................................. 128/222
16513  of 1900  United Kingdom .................. 128/223

OTHER PUBLICATIONS

*Science,* Jun. 28, 1946, p. 759.

*Primary Examiner*—Robert W. Michell
*Assistant Examiner*—C. F. Rosenbaum
*Attorney, Agent, or Firm*—Albert L. Jeffers; Roger M. Rickert

[57] ABSTRACT

Method and apparatus for force-feeding a patient despite a swallowing impairment is disclosed and includes a feeding tube which may be passed through the patient's nasal cavity and by way of the pharynx sufficiently far into the stomach to allow foodstuff or like material emanating from the tube to enter the patient's stomach. The feeding tube extends from a material outlet on a dispensing container which has a further air inlet. The material may be placed in the container so that upon increasing the air pressure within the container, material is forced therefrom by way of the tube to the patient. A source of air at a pressure greater than the ambient atmospheric pressure provides the pressure increase and includes a bleeder valve for regulating the rate of air flow from the pump to the container thereby also regulating the material flow through the tube.

5 Claims, 7 Drawing Figures

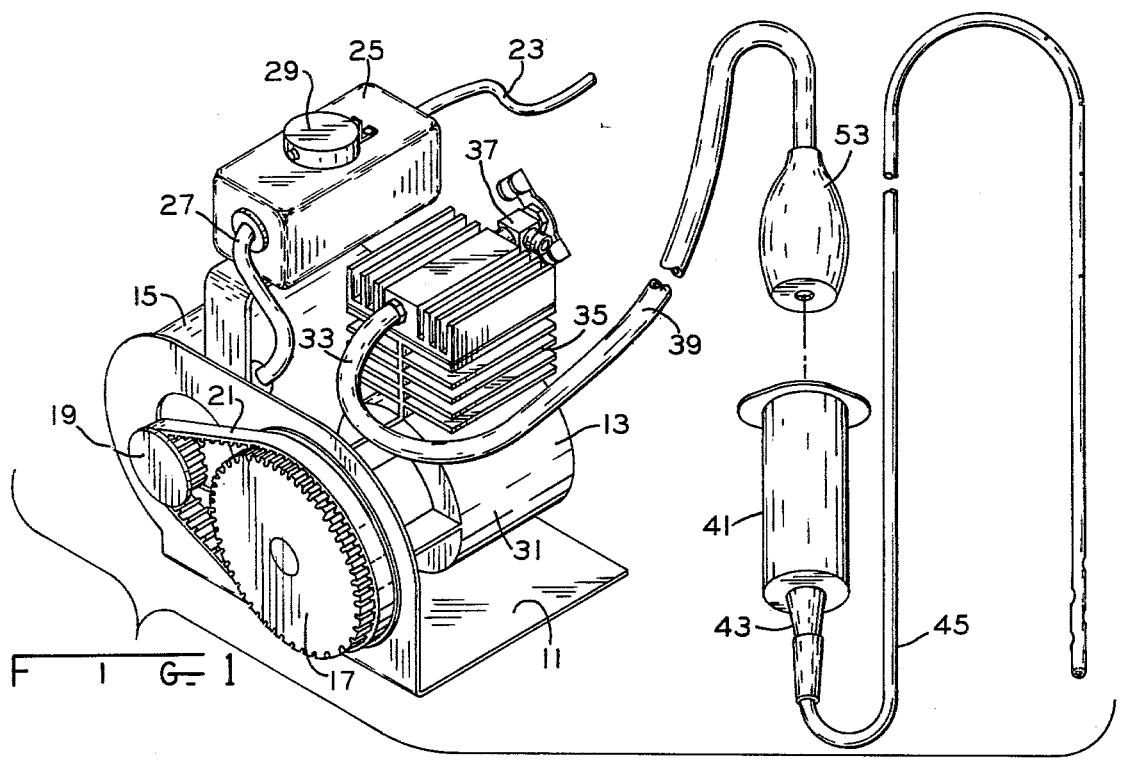
FIG. 1
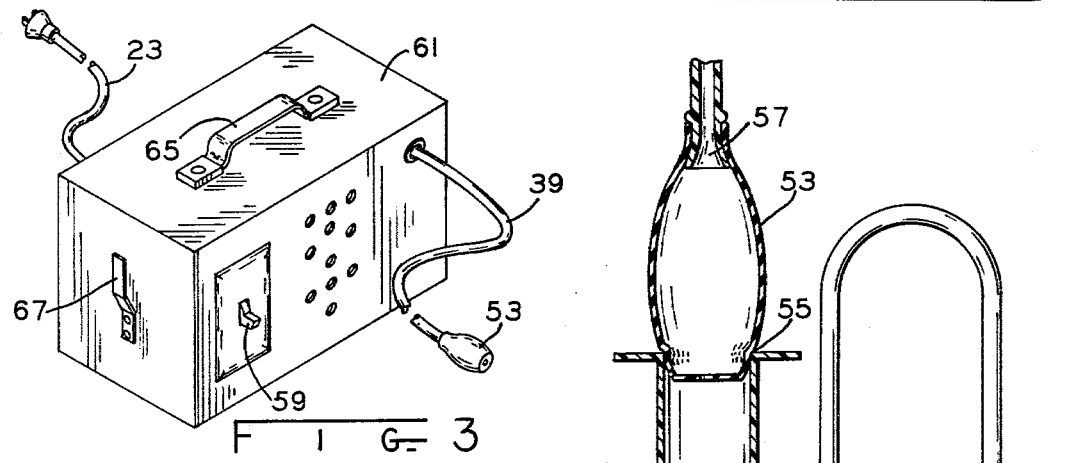
FIG. 3
FIG. 2
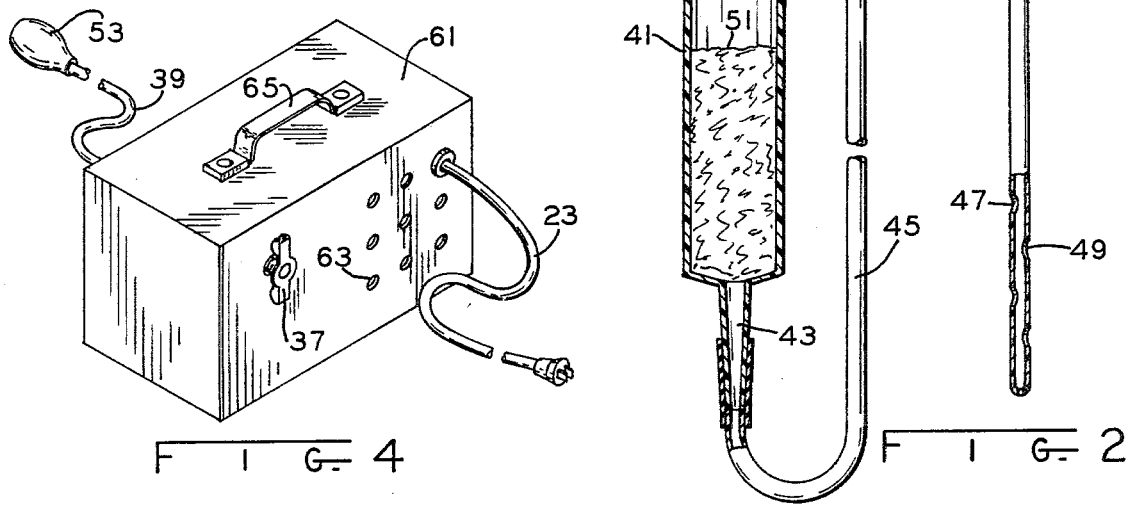
FIG. 4

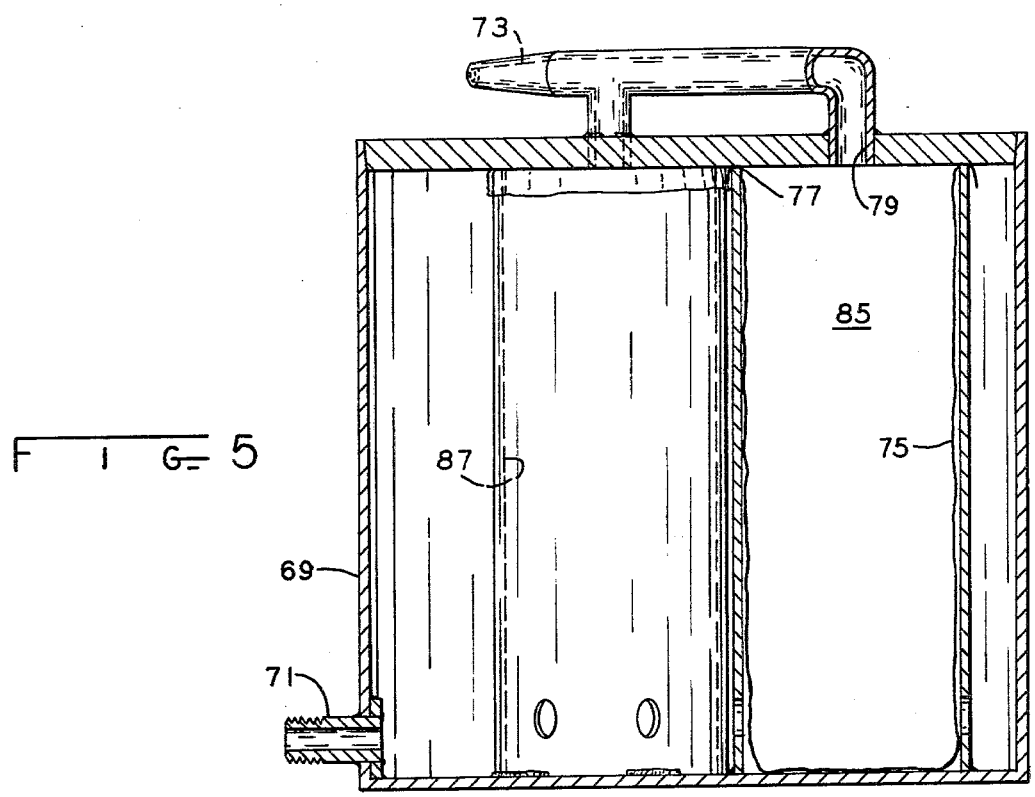
FIG 5
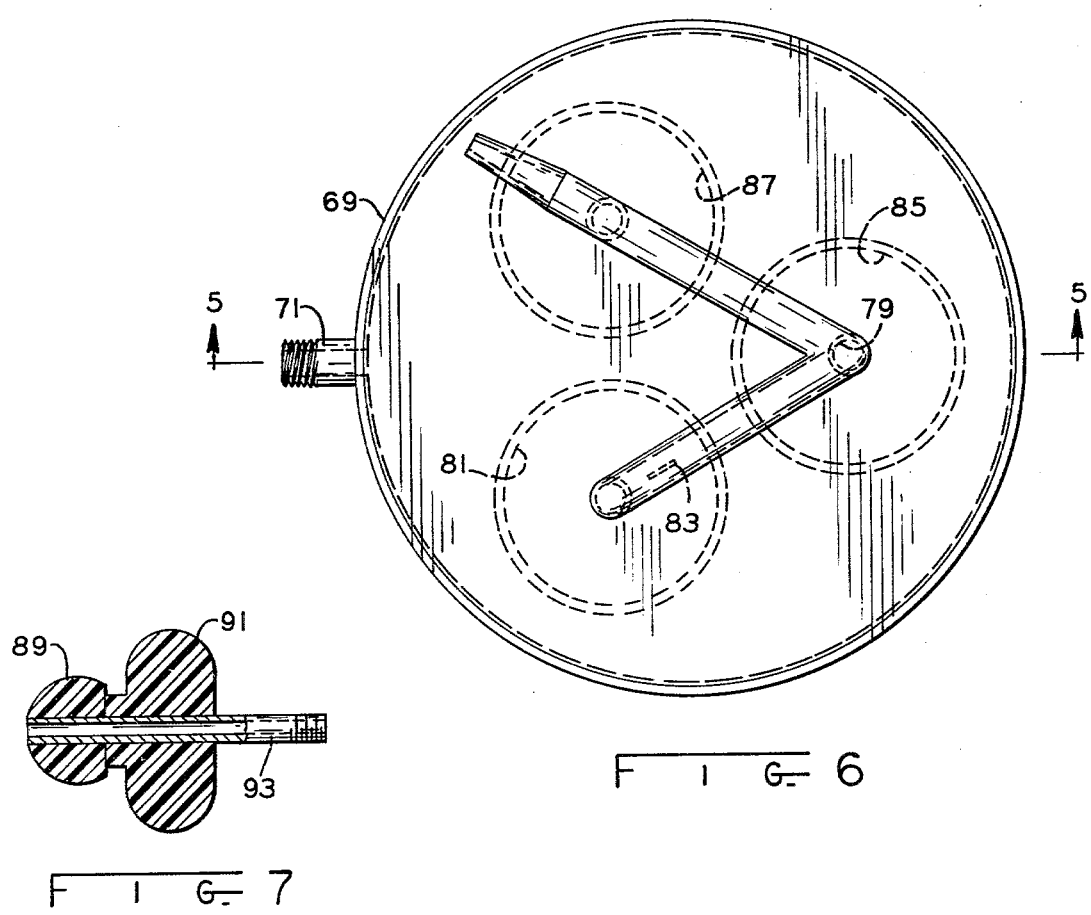
FIG 6
FIG 7

AIR PUMPING FOR MEDICAL USES

BACKGROUND OF THE INVENTION

The present invention relates generally to a method and apparatus for dispensing materials and more particularly to a scheme whereby a patient may be force-fed despite a swallowing impairment, and to an air pump arrangement suitable for such force-feeding, and for other patient treatment purposes which may on occasion be used in a potentially flammable environment.

In emergency or operating rooms of hospitals it is not uncommon to encounter potentially flammable environments, for example when ether or oxygen are in use. While adequate safety guards are usually provided for these potentially flammable materials, an added safety margin accrues by using only arc or spark-free equipment in such environments.

Further, in the general medical arts, it may occur that a patient has a swallowing impairment due to any of a wide variety of reasons, such as unconsciousness, a stroke, paralysis of the esophagus or other peristalic dysfunctions requiring either intravenous feeding or feeding of a comestible material by way of a naso-gastric tube. An air pump may be advantageously employed for such force-feeding, and may also provide other patient treatment functions, including but not limited to urological irrigation.

Typically, swallowing impairments are bypassed by a naso-gastric feeding tube, with the flowable foodstuff being supplied thereto from a dispensing device solely by gravity flow. With such a gravity system, feeding is quite slow, with a typical meal requiring one-half hour or more to administer. Similarly, with a gravity flow system, tube or tube opening blockage occurs frequently, requiring removal of the feeding tube from the patient, and of course such a gravity feeding system is less liable to blockage and more readily administered when relatively thin watery foodstuffs are employed. Relatively viscous and not easily flowable nutrients are extremely difficult to administer, using such a gravity system.

The known prior art force-feeding arrangements also require the resterilization or replacement of numerous component parts, including the dispenser or container, subsequent to each feeding operation, and are in general not well suited to home use by the patient.

SUMMARY OF THE INVENTION

Among the several objects of the present invention may be noted the provision of a portable air compressor assembly suitable for a wide range of patient uses; the provision of a portable air compressor assembly operable in a discharge or spark-free manner, and therefore operable safely in a potentially flammable environment, for example in the presence of ether or oxygen; the provision of a method and apparatus for feeding a flowable foodstuff or like material to a patient with a swallowing impairment; and the provision of a force-feeding arrangement for rapidly and positively circumventing a patient's normal swallowing apparatus. These as well as other objects and advantageous features of the present invention will be in part apparent and in part pointed out hereinafter.

In general, a method of force-feeding a patient includes passing a hollow tube through the patient's nasal cavity and by way of his pharynx sufficiently far down into the stomach to allow material emanating from the tube near one end thereof to enter the patient's stomach. Material to be fed to the patient is placed in a relatively rigid container and the pressure within the container is increased by adding air to displace material from the container into the tube and to the patient.

This pressure increase may be achieved by operating a power driven compressor throughout the feeding process and supplying the compressor air output to the container with a portion of the compressor air output being diverted directly into the atmosphere to thereby control the amount of air supplied to the container and therefore also the rate at which material is supplied from the container to the patient. The material may initially be disposed in a pliable container with the pliable container being placed within the rigid container, and an air input to the rigid container outside the pliable container is established to displace material from the pliable container by way of a material outlet to the patient. The rigid container is maintained airtight except for the air inlet and material outlet.

Also in general and in one form of the invention, a naso-gastric feeding device includes a dispensing container with an air inlet and a material outlet having a feeding tube extending from the material outlet with openings near the remote end thereof for conveying material from the container to a patient's stomach. The container air inlet is connected to a source of air at a pressure greater than ambient atmospheric pressure to insure the flow of material from the dispensing container to the patient, and this air pressure source is regulated to thereby also regulate the material flow rate through the tube. The container during operation may be disposed with the material outlet near the bottom thereof and may further include a selectively sealable opening for recharging the container with material. A removable stopper may close this material-receiving opening, and the air inlet may be disposed in the stopper. In the alternative, a disposable pliable container may initially store the material, be placed into the dispensing container and connected to the material outlet, and thereafter collapsed by air entering the dispensing container to displace the material from the pliable container by way of the material outlet into the feeding tube. A plurality of such disposable pliable containers may be disposed within the dispensing container sharing the material outlet, and valving arrangements may be provided for controlling the egress of material from certain ones of those pliable containers.

Still further in general and in one form of the invention, an air pump for patient treatment which may be disposed in a potentially flammable environment includes a contact free electric motor with an air compressor coupled in driven relation thereto and having a low pressure filtered air inlet and a high pressure outlet. An encapsulated power switch for selectively enabling and disabling the motor is operator accessible as is an air bleed valve for selectively diverting part of the compressor air output from the high pressure outlet to the ambient atmosphere so that the air pump may be energized and its output adjusted to a preferred value without any exposed electrical discharge occurring.

BRIEF DESCRIPTION OF THE DRAWINGS

FIG. 1 is a perspective view of a pneumatic naso-gastric feeding device in one form of the invention;

FIG. 2 is a view partially in cross-section of the dispensing container and feeding tube of FIG. 1;

FIG. 3 is a perspective view of a modified air pump according to the present invention;

FIG. 4 is a perspective view of the modified air pump of FIG. 3, showing the sides opposite those illustrated in FIG. 3;

FIG. 5 is a side view in cross-section of a dispensing container employing a plurality of disposable liners;

FIG. 6 is a top view of the dispensing container of FIG. 5; and

FIG. 7 is a side view in cross-section of an alternate stopper for the dispensing containers of FIGS. 1 and 2.

Corresponding reference characters indicate corresponding parts throughout the several views of the drawing.

The exemplifications set out herein illustrate a preferred embodiment of the invention in one form thereof and such exemplifications are not to be construed as limiting the scope of the disclosure or the scope of the invention in any manner.

DESCRIPTION OF THE PREFERRED EMBODIMENTS

Referring now to the drawing and in particular to FIG. 1, an air pump arrangement for patient treatment with the exterior housing thereof removed is illustrated and seen to include a base 11 supporting a compressor 13 and an electric motor 15, provided respectively with pulleys or toothed wheels 17 and 19, and drivingly interconnected by toothed belt 21. Power cord 23 may be connected to a conventional wall outlet or other source of electrical energy and passes into speed controller housing 25, which may contain a rheostat, variable reactance or other control arrangement for supplying selectively reduced power by way of cable 27 to the motor 15. The speed controller, which is actuable by knob 29, may for example be the simple commercially available light dimmer switch employed in home lighting arrangements.

Compressor 13 which is driven by the speed reducing power drive including the toothed wheels 19 and 17 and interconnecting belt 21 may, for example, be of a relatively small conventional piston compressor design having an air inlet on the rear face of the lower crankcase portion 31, which air inlet may include a conventional air filter and having an air outlet 33 near the top piston portion 35 of the compressor. The air outlet may also be directed by way of a bleeder valve 37 directly to the atmosphere to control the quantity of air displaced by the compressor by way of tube 39.

The dispensing container 41 is a relatively rigid container as illustrated in FIGS. 1 and 2, having a material outlet 43 near the bottom thereof, which material outlet is connected to feeding tube 45. The feeding tube 45 is of a length sufficient to be passed through a patient's nasal cavity and by way of his pharynx sufficiently far into the stomach to allow material emanating from the tube openings, such as 47 and 49, to enter the patient's stomach. Material, such as a flowable foodstuff within the dispensing container 41 is, due to the attitude of the container and the gravitational effect on the material, disposed in the dispenser as viewed. A rubber bulb-like stopper 53 may be removed from the container 41 to replenish the material supply therein and when stopper 53 is replaced in the container 41 an airtight seal around the rim region 55 is achieved so that air being supplied by way of tube 39 to an air inlet region 57 in the stopper increases the pressure above the interface 51, forcing material by way of the material outlet 43 to the patient.

While the multi-outlet gastro tube is in standard use, a simple flow through tube with an end outlet only is adequate and desirable for this system and is recommended for the patient who inserts it himself for each feeding. The elimination of the side holes decreases nasal irritation during insertion and removal of the tube when such operation is done frequently.

As described in reference to FIG. 1, the motor 15 was a universal motor, rheostat controlled, so that no on-off switch was really required. As depicted in FIGS. 3 and 4, rheostat or speed control 25 has been deleted, and an on-off switch 59 has been added. The motor within housing 61 may, if desired, be a contact free variety such as a shaded pole motor, thereby eliminating sparks such as may occur in a motor having brushes or a starting switch. If use of the air pump of the present invention may occur in a potentially flammable environment, such as the aforementioned operating or emergency room, where ether and/or oxygen may be in use, elimination of this source of arcing is highly desirable. The on-off switch 59 may be of the mercury tilt or Reed switch variety or another type of encapsulated power switch, so that enabling and disabling the motor also occurs in an arc free manner, thereby making the unit safe for use in the potentially flammable environment. The air pump of FIGS. 3 and 4 may otherwise be identical to that depicted in FIG. 1, with the air bleed valve 37, which selectively diverts part of the air output from the compressor directly to the atmosphere, forming the only control for adjusting the pump air output to a preferred value.

Housing 61 may further include air inlet holes, such as 63, having an additional air filter therebehind, through which the air must pass prior to entering the compressor. The housing further includes a carrying handle 65 and a bracket 67 about which the air outlet tube 39 and power cord 23 may be wrapped for convenience when the air pump is transported from one location to another.

An arrangement for maintaining the air within the dispensing container separate from the material within the dispensing container is depicted in FIGS. 5 and 6. With this arrangement the rigid container 69 has an air inlet 71 and a material outlet 73, but is otherwise relatively air-tight and relatively rigid. A disposable pliable container, such as 75, initially stores the material to be dispensed, and when placed in the dispensing container 69, is connected to the material outlet 73, for example by an airtight seal, around the upper rim 77 with the material communicating with the material outlet by way of opening 79. Air entering the dispensing container collapses the pliable container 75, thereby displacing the material from the pliable container by way of the material outlet to a feeding tube, as previously described. Several such pliable inner containers may be employed and, for example, compartments for three such containers are depicted in FIG. 6 with two of these containers being, for example, eight ounce food containers while the third container 81 may simply contain water.

During the feeding process, a valve such as 83 may be closed to insure that the food containers 85 and 87 are emptied by the incoming air, and thereafter valve 83 may be opened to displace the water from pliable container 81 through the feed tube to displace the remaining foodstuff from the tube, as well as aiding in cleaning the system. Any desired arrangement of disposable pliable containers having a variety of material and valving arrangements is possible and if a plurality of valves are employed, any desired feeding sequence is possible.

An alternative to the bulb stopper 53, depicted in FIGS. 1 and 2, is illustrated in FIG. 7, having a soft rubber or plastic sealing region 89 and a relatively more rigid molded plastic hand-gripping portion 91, through which an air inlet tube 93 for connection to the pump output tube 39 may pass. Thus, the stopper depicted in FIG. 7 could replace the stopper 53 of FIGS. 1 and 2. A combination of the concepts illustrated in FIGS. 1 and 2, and those illustrated in FIGS. 5 and 6, is also implemented by a stopper of the type depicted in FIG. 7. Using the same dispensing container 41, a disposable pliable bottle liner containing the foodstuff might be inserted into dispensing container 41 with the open top thereof disposed about rim 55. Feeding tube 45 could be coupled to the stopper tube 93 with the air source, such as compressor output tube 39, being coupled to the lower former material output region 43 of the dispensing container. Energization of the compressor would then displace material from the pliable liner upwardly through tube 93 and to the patient, with the soft plastic seal 89 not only sealing the dispensing container but also firmly gripping the upper edges of the liner to make a sealing connection therewith.

From the foregoing it is now apparent that a novel patient feeding process and apparatus, as well as a novel air pump for patient treatment purposes, has been disclosed meeting the objects and advantageous features set out hereinbefore as well as others, and the modifications as to the precise configurations, shapes and details, as well as the precise steps of the method, may be made by those having ordinary skill in the art without departing from the spirit of the invention or the scope thereof as set out by the claims which follow.

WHAT IS CLAIMED IS:

1. The method of force feeding a patient comprising the steps of:

passing a tube through the patient's nasal cavity and, by way of the pharynx, sufficiently far into the stomach to allow material emanating from the tube to enter the patient's stomach;

placing a material to be fed to the patient in a relatively rigid container;

increasing the pressure within the container by adding air to the air side of the air-material interface to displace material from the container into the tube and to the patient.

2. The method as set forth in claim 1 wherein the step of increasing the pressure includes operating a power driven compressor throughout the feeding process, supplying the compressor air output to the container, and diverting part of the compressor air output directly into the atmosphere to thereby control the amount of air supplied to the container and therefore also the rate at which material is supplied to the patient.

3. The method as set forth in claim 1 wherein the steps of placing and defining include enclosing the material within a pliable container, placing the pliable container within the rigid container, establishing an air inlet to the rigid container outside the pliable container, and establishing a material outlet from the pliable container through the rigid container to the tube with the rigid container being maintained airtight except for the said air inlet and material outlet.

4. The method as set forth in claim 3 wherein a plurality of dissimilar materials may be enclosed within a like plurality of pliable containers and the plurality of pliable containers all be placed concurrently within the rigid container, the step of establishing a material outlet including sequentially connecting the tube to different pliable containers to sequentially supply material from the different pliable containers.

5. The method as set forth in claim 4 wherein one connected pliable container is substantially emptied before another pliable container is connected to the tube.

* * * * *